United States Patent [19]
Hotta et al.

[11] Patent Number: 5,707,503
[45] Date of Patent: Jan. 13, 1998

[54] OXYGEN SENSOR ELEMENT

[75] Inventors: Yasumichi Hotta, Mie-gun; Hiromi Sano, Nagoya; Toshitaka Saito, Toyohashi; Masatoshi Suzuki, Nagoya; Naoto Miwa, Tsushima, all of Japan

[73] Assignee: Nippondenso Co., Ltd., Kariya, Japan

[21] Appl. No.: 549,209

[22] Filed: Oct. 27, 1995

[30] Foreign Application Priority Data

Oct. 28, 1994 [JP] Japan .................... 6-289092

[51] Int. Cl.⁶ .................................. G01N 27/26
[52] U.S. Cl. ............... 204/426; 204/424; 205/163; 205/167; 205/210; 205/219
[58] Field of Search .................. 204/421, 424, 204/425, 426, 427, 429; 205/163, 167, 210, 219

[56] References Cited

U.S. PATENT DOCUMENTS

| | | | |
|---|---|---|---|
| 4,220,516 | 9/1980 | Sano et al. | 204/428 |
| 4,650,697 | 3/1987 | Kitagawa et al. | 427/125 |
| 4,851,105 | 7/1989 | Ishiguro et al. | 204/429 |
| 4,863,583 | 9/1989 | Kurachi et al. | 204/424 |
| 5,021,304 | 6/1991 | Ruka et al. | 429/30 |
| 5,421,984 | 6/1995 | Saito et al. | 204/426 |

FOREIGN PATENT DOCUMENTS

| | | |
|---|---|---|
| 372425 | 6/1991 | European Pat. Off. |
| 3804683 | 8/1988 | Germany |
| 3813930 | 11/1988 | Germany |
| 4342064 | 6/1994 | Germany |
| 4401749 | 7/1994 | Germany |
| 53-10491 | 1/1978 | Japan |
| 53-29191 | 3/1978 | Japan |
| 55-33019 | 8/1980 | Japan |

*Primary Examiner*—Bruce F. Bell
*Attorney, Agent, or Firm*—Cushman, Darby Cushman IP Group of Pillsbury Madison & Sutro LLP

[57] ABSTRACT

According to the present invention, an oxygen sensor element includes a solid electrolyte having a side surface at one side thereof, the side surface being contactable with a gas to be measured, a skeletal electrode provided on the side surface and having a plurality of pore portions, each of the pore portions passing through the skeletal electrode up to the solid electrolyte, and a reactive electrode made of a porous film and provided in each of the pore portions, a thickness of the porous film being smaller than that of said skeletal electrode. An area percentage (SH/SZ) which is a ratio of a total area (SH) of the reactive electrode to a total area (SZ) of the skeletal electrode and the reactive electrode is in a range from 10 to 50%, an average area (SA) of the pore portions is 100 μm² or less, a film thickness of the skeletal electrode is in a range from 1.5 to 4 μm, and the film thickness of the reactive electrode is in a range from 0.6 to 1.5 μm. The oxygen sensor element is superior in the heat resistance characteristics and the response characteristics.

18 Claims, 6 Drawing Sheets

OXYGEN SENSOR ELEMENT

CROSS REFERENCE TO RELATED APPLICATION

The present invention is based on and claims priority from Japanese applications No. 6-289092 filed on Oct. 28, 1994, the content of which is incorporated herein by reference.

BACKGROUND OF THE INVENTION

1. Field of the Invention

The present invention relates to an oxygen sensor element used mainly for air-fuel ratio control of an automobile engine or the like.

2. Related Art

Recently, with changes in the environment for an automobile engine and strengthening of exhaust gas regulations, higher levels of durability have been demanded for oxygen sensor elements applied to automobile engines and the like. In order to achieve such high durability, it is necessary, in the oxygen sensor element, to improve the heat resistance characteristic of the electrode at the side of the gas to be measured.

As methods for manufacturing the above-mentioned electrode, chemical plating, sputtering, paste printing, etc. are generally employed. However, since electrodes manufactured by chemical plating or sputtering are thin, such electrodes are ablated and exfoliated within a short time period, although having superior response characteristic. For this reason, such electrodes are inferior in their heat resistance characteristic. On the other hand, since an electrode formed by paste printing is a thick film, this electrode is inferior in the response characteristic although being superior in its heat resistance characteristic. Thus, the response characteristic and the heat resistance characteristic in the oxygen sensor element are contrary to each other and it is difficult to obtain both characteristics in one element.

To overcome this problem, an oxygen sensor element 9 illustrated in FIG. 9 has been proposed.

In this oxygen sensor element 9, an auxiliary lead 91 is formed on the surface of a solid electrolyte 90 at the side of the gas to be measured in the form of a mesh by using a platinum paste containing glass or a ceramic aggregate, and thereafter a thin film electrode 92 is formed on the surfaces of the auxiliary lead 91 and the solid electrolyte 90 by chemical plating (Japanese Examined Patent Publication No. Sho. 55-33019).

In the above-mentioned oxygen sensor element 9, since the thickness of the thin film electrode 92 is thin, a high response characteristic can be obtained. Further, since the thickness of the auxiliary lead 91 is thick, the heat resistance is high. Also, even if a part of the thin film electrode 92 is ablated and exfoliated and the thin film electrode 92 is fractured, the conductivity between the fractured pieces thereof can be ensured by the auxiliary lead 91.

In the oxygen sensor element, a thin film electrode reinforcing portion for reinforcing the thin film electrode can also be provided on the surface of this thin film electrode by sputtering or the like (Japanese Unexamined Patent Publication No. Sho. 53-29191).

However, in the above-mentioned conventional techniques as well, particularly under bad conditions such as when the temperature of the exhaust gas is high, there still may be problems in that the heat resistance and response characteristics of the oxygen sensor element are insufficient.

That is, as illustrated in FIG. 10, in the former of the above-mentioned oxygen sensor elements 9, the thin film electrode 92 is aggregated in the interior of a grating 910 formed by the auxiliary lead 91 and becomes aggregated pieces 920 in the form of islands. In such a case, the auxiliary lead 91 cannot prevent electrical disconnection thereof from the thin film electrode 92, which results in that the output of the thin film electrode 92 cannot be taken out.

In the latter of the above-mentioned oxygen sensor elements, from the viewpoint of the necessity to ensure the response characteristic, it is not possible to increase the total film thickness of the thin film electrode and the electrode reinforcing portion to such an extent as to enable a sufficient heat resistance characteristic to be ensured.

SUMMARY OF THE INVENTION

The present invention has been made in view of the above-mentioned problems, and an object of the present invention is to provide an oxygen sensor element having both an excellent heat resistance characteristic and an excellent response characteristic, and a method for manufacturing the same.

In order to obtain the above object, according to a first aspect of the present invention, an oxygen sensor element includes a solid electrolyte having a side surface at one side thereof, the side surface being contactable with a gas to be measured, a skeletal electrode provided on the side surface and having a plurality of pore portions, each of the pore portions passing through the skeletal electrode up to the solid electrolyte, and a reactive electrode made of a porous film and provided in each of the pore portions, a thickness of the porous film being smaller than that of said skeletal electrode. An area percentage (SH/SZ) which is a ratio of a total area (SH) of the reactive electrode to a total area (SZ) of the skeletal electrode and the reactive electrode is in a range of from 10 to 50%, an average area (SA) of the pore portions is 100 μm$^2$ or less, a film thickness of the skeletal electrode is in a range from 1.5 to 4 μm, and the film thickness of the reactive electrode is in a range from 0.6 to 1.5 μm.

When the area percentage (SH/SZ) is below 10%, the surface of the solid electrolyte is substantially covered with the skeletal electrode having a large film thickness. Therefore, the response characteristic of the oxygen sensor element may be deteriorated. On the other hand, when the area percentage is over 50%, the skeletal electrode is divided into several pieces and separated from each other. Therefore, it may be difficult to prevent the coagulation of the reactive electrode.

The average area (SA) of the pore portions is preferably 100 μm$^2$ or less. When this average area (SA) is over 100 μm$^2$, the reactive electrode aggregates in the form of island shape within the pore portions. In such a case, the reactive electrode may be electrically disconnected, and the conductivity between the skeletal electrode and the reactive electrode may be deteriorated.

The film thickness of the skeletal electrode is preferably in a range from 1.5 to 4 μm and the film thickness of the reactive electrode is preferably in a range from 0.6 to 1.5 μm.

When the film thickness of the skeletal electrode is below 1.5 μm, since the heat resistance characteristic is insufficient, the skeletal electrode may not function sufficiently. When this film thickness is over 4 μm, the cost of forming the skeletal electrode may increase. Also, even if the thickness of the skeletal electrode gets larger than this value, the improvement of the performance of the oxygen sensor element cannot be obtained.

When the thickness of the reactive electrode is below 0.6 μm, the reactive electrode easily aggregates. On the other hand, when this thickness is over 1.5 μm, the response characteristic of the oxygen sensor element may be deteriorated.

It is preferable that the surface of the solid electrolyte at the side of the gas to be measured having a surface roughness Rz of from 30 to 60 μm.

In this way, the adhesion strength of the skeletal electrode and the reactive electrode to the solid electrolyte increases. In addition, the coagulation of the reactive electrode can be suppressed by an anchor effect.

The above-mentioned surface roughness values are those under the Japanese Industrial Standard "Ten-Point Average Roughness". When the surface roughness is below 30 μm, the adhesion strength of the skeletal electrode and reactive electrode to the solid electrolyte may be deteriorated. On the other hand, when the surface roughness is over 60 μm, the film thickness may vary largely when forming the skeletal electrode, etc., thereby the characteristics of the oxygen sensor element being unstable.

Preferably, the reactive electrode is formed on the skeletal electrode as well. In such a case, when manufacturing the oxygen sensor element, it is possible to form the reactive electrode on the entire surface (including the surface of the skeletal electrode) of the solid electrolyte, where the skeletal electrode is provided, by chemical plating, sputtering, platinate applying and reducing/baking, or the like. Thus, the method for manufacturing the oxygen sensor element is simplified. Although, in such a case, the oxygen sensor element has the reactive electrode formed on the skeletal electrode, in the present invention, such reactive electrode portion corresponds to a part of the skeletal electrode.

Also, it is preferable that a protective layer be provided on the surfaces of the skeletal electrode and reactive electrode and that a trap layer be further provided on the surface of the protective layer.

Further, the solid electrolyte can be of various shapes such as, for example, cup-shaped, plate-shaped, etc.

According to a second aspect of the present invention, a method of manufacturing an oxygen sensor element having a solid electrolyte, the method includes a step of forming a first metal film on a surface of the solid electrolyte at the side of a gas to be measured, a step of forming pore portions on the first metal film by coagulating the first metal in such a manner that the pore portions pass from a surface of the first metal film to the solid electrolyte, and a step of forming a second metal film on the surface of the first metal film, which have been covered with the pore portions.

As the above-mentioned first and second metal films, platinum, rhodium, palladium, iridium, or the like, or alloyed mixtures of these metals can be used.

The first and second metal films can be formed by, for example, chemical plating, electrical plating, or sputtering or the like, or combinations of these techniques.

It is preferable that the first metal film having a thickness from 0.6 to 1.5 μm.

When the thickness of the first metal film is below 0.6 μm, the amount of metal is small and the skeletal electrode may be divided. On the other hand, when the thickness is over 1.5 μm, the cost of forming the skeletal electrode may increase. Furthermore, the improvement of the performance of the oxygen sensor element corresponding to the cost increase, cannot be obtained.

The heating for the coagulation of the first metal film is preferably performed at a high temperature that prevents the skeletal structure from being re-aggregated during the operation of the oxygen sensor element.

The heating temperature depends on the kind of the metal film and the conditions where the oxygen sensor element is used. For example, when the first metal film is made of platinum, it is preferable that this first metal film be heated at a temperature from 1100° to 1300° C. When the temperature is below 1100° C., densification of the platinum is not good enough, which results in the skeletal electrode may not function sufficiently. In addition, no pore portions may be formed. When the temperature is over 1300° C., the platinum is excessively aggregated and divided into separate pieces in the form of island shape. At this time, the skeletal electrode is divided and fractured into separate pieces, and the coagulation of the reactive electrode may not be able to be prevented.

In order to use the above-mentioned oxygen sensor element for controlling the air-fuel ratio of an engine of an automobile, it is necessary to perform the heating for the coagulation of the first metal film at a temperature sufficiently higher than 950° C., which is the maximum temperature of the exhaust gas. When being formed at the lower temperature, the skeletal electrode may be re-aggregated during the operation, thereby being divided into separate pieces.

In the pore portions, the solid electrolyte is exposed and there is no skeletal electrode. The second metal film in the pore portions serves as the reactive electrode. Accordingly, when the above-mentioned area percentage (SG/SK) is below 10%, the surface of the solid electrolyte is substantially wholly covered by the skeletal electrode having a large film thickness, and the response characteristic of the oxygen sensor element may be deteriorated. On the other hand, when the area percentage is over 50%, the respective portions of the skeletal electrode may be divided into separate pieces, and the coagulation of the reactive electrode may not be able to be prevented.

It is preferable that a roughening treatment for a surface roughness Rz ranging from 30 to 60 μm be performed on the surface of the solid electrolyte at the side of the gas to be measured and that etching treatment be subsequently performed on the surface of the solid electrolyte, before the first metal film is formed.

As mentioned above, the adhesion strength of the skeletal electrode and the reactive electrode adhere to the solid electrolyte increases, because a concave and convex portion is formed on the surface of the solid electrolyte. Further, the coagulation of the reactive electrode can be suppressed by an anchor effect.

The reasons for setting the upper and the lower limit of the above-mentioned surface roughness are the same as mentioned above.

A protective layer made of a heat-resisting metal oxide is preferably provided on the surface of the reactive electrode. Thus, it is possible to sandwich the reactive electrode and the skeletal electrode between the solid electrolyte and the protective layer, so that the durability of the reactive electrode and skeletal electrode is improved.

Each of the pore portions having an area of 100 μm$^2$ or less preferably occupies 80% or more of the number of all the pore portions.

When the pore portions are below 80% of the number of all the pore portions, a larger number of the reactive electrode pieces are provided at the pore portions, each of which has an area of 100 μm$^2$ or more. For this reason, the reactive electrode may be aggregated, thereby the response characteristic of the oxygen sensor element being deteriorated.

Further, the area percentage (SH/SZ) which is the ratio of the total area (SH) of the reactive electrode provided at the pore portions, each of which has an area of 100 µm² or less to the total area (SZ) of the skeletal electrode and the reactive electrode provided at the pore portions, each of which has an area of 100 µm² or less is in a range from 10 to 50%.

When this area percentage (SH/SZ) is below 10%, since the surface of the solid electrolyte is substantially wholly covered by the skeletal electrode having a large thickness, the response characteristic of the oxygen sensor element may be deteriorated. On the other hand, when the area percentage is over 50%, respective portions of the skeletal electrode may be divided into separate pieces, and the coagulation of the reactive electrode may not be prevented.

BRIEF DESCRIPTION OF THE DRAWINGS

Additional objects and advantages of the present invention will be more readily apparent from the following detailed description of preferred embodiments thereof when taken along together with accompanying drawings in which:

FIGS. 6A and 5B are views illustrating a second process step for manufacturing the oxygen sensor element;

DETAILED DESCRIPTION OF THE PREFERRED EMBODIMENTS

An oxygen sensor element according to a first embodiment of the present invention and an oxygen sensor which employs this oxygen sensor element will now be described with reference to FIGS. 1 to 4.

Figure 1:
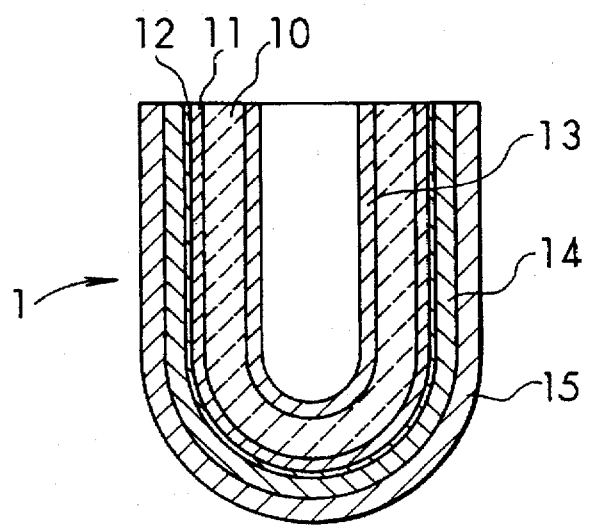
FIG. 1 is a sectional view illustrating an oxygen sensor element according to an embodiment of the present invention.
Figure 2:
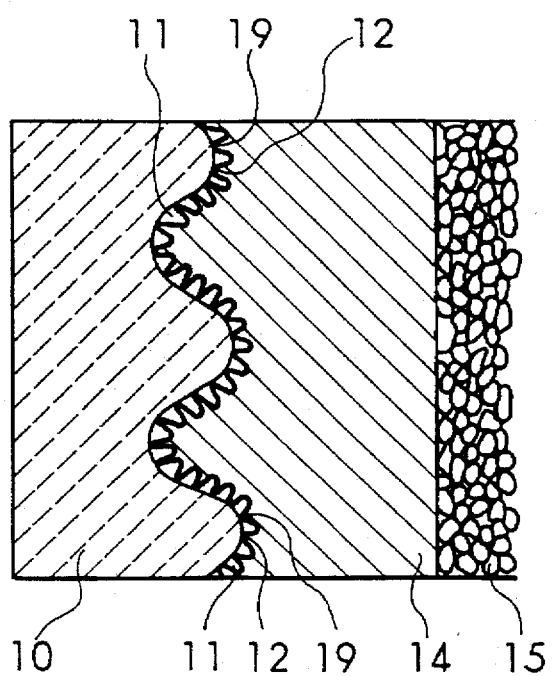
FIG. 2 is a sectional view illustrating an essential portion of the oxygen sensor element according to the embodiment of the present invention.
Figure 3:
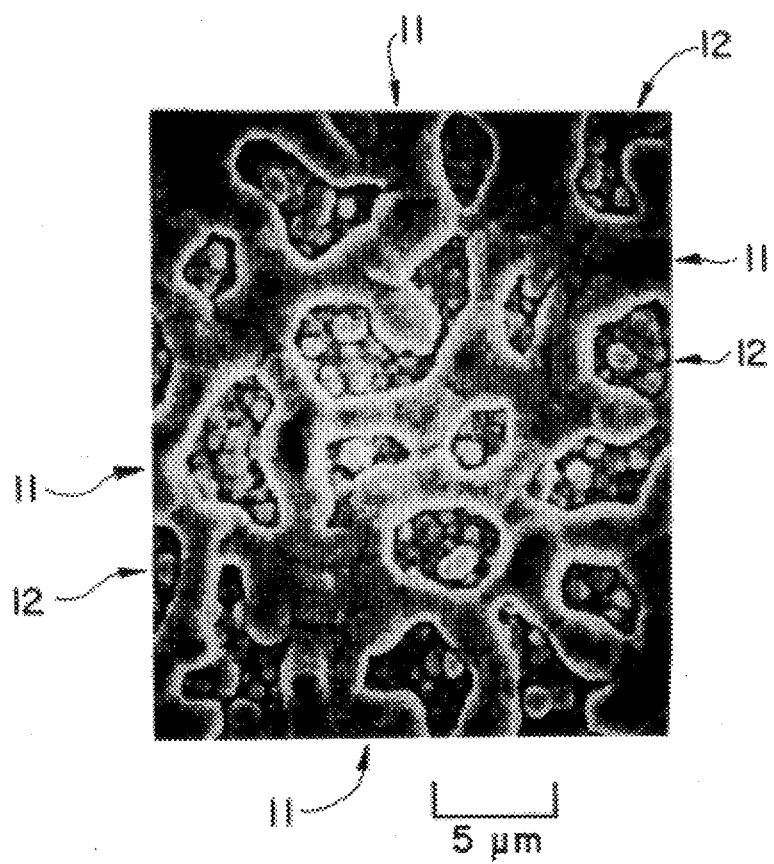
FIG. 3 is an SEM photograph showing a metallic particle structure of reactive electrode and the skeletal electrode surfaces in the embodiment of the present invention.

Firstly, as illustrated in FIGS. 1 and 2, an oxygen sensor element 1 according to the first embodiment comprises a protruded conductive skeletal electrode 11 on the surface at the side of the gas to be measured, of a cup-shaped solid electrolyte 10. Further, the oxygen sensor element 1 also comprises pore portions 19 between the skeletal electrode, and the solid electrolyte is exposed in the pore portions 19. A reactive electrode 12 is formed on the surface of the pore portions 19 to cover the pore portions 19 (FIG. 3).

The skeletal electrode 11 may be formed on only a tip end of the solid electrolyte 10, which is the hottest in temperature during the use of the oxygen sensor element 1, and the reactive electrode 12 may be formed extending over the remaining area.

The pore area (SP) of each of the pore portions 19 is set to have a predetermined size in such a manner that the electrical disconnection of the reactive electrode 12 from the skeletal electrode 11 is prevented even when the reactive electrode 12 on each pore portion 19 has been aggregated by heating.

Further, the reactive electrode 12 is a porous film made of platinum, and the skeletal electrode 11 is a platinum film which has been dense by the heat treatment performed in a second embodiment, which will be described later. The area percentage (SH/SZ) which is the ratio of the total area (SH) of the reactive electrode 12 to the total area (SZ) of all electrodes including the skeletal electrode 11 and the reactive electrode 12 is 30%.

Further, the average area (SA) of the pore portions 19 is 18 µm², the film thickness of the skeletal electrode 11 is 1.9 µm, and the film thickness of the reactive electrode 12 is 0.8 µm.

FIG. 3 shows a photograph of the surfaces of the skeletal electrode 11 and the reactive electrode 12 taken by a scanning-type electron microscope. In FIG. 3, a mesh-like portion (the portion appearing to be floating up from the drawing sheet) is the skeletal electrode 11, and the reactive electrode 12 composed of dotted fine particles can be observed within the skeletal electrode. These fine particles are platinum particles that have been formed along the sintered particles of the solid electrolyte 10.

On the surfaces of the skeletal electrode 11 and the reactive electrode 12, as illustrated in FIG. 1, a protective layer 14 and a trap layer 15 for covering the protective layer are provided. The protective layer 14 is made of a $MgO \cdot Al_2O_3$ spinel, and the trap layer is composed of particles of $\gamma\text{-}Al_2O_3$ or the like.

The surface of the protective layer 14 preferably has a porosity of from 4 to 13%. When this porosity is below 4%, the diffusion resistance of the exhaust gas gets high, and that the response characteristic of the oxygen sensor element may be deteriorated. On the other hand, when the porosity is over 13%, a sufficient effect for protecting the electrode cannot be obtained.

As the above-mentioned heat-resisting metal oxide, other than $MgO \cdot Al_2O_3$ spinel, for example, $Al_2O_3$, $ZrO_2$, or the like, or mixtures of these materials can be used.

The thickness of the protective layer 14 is preferably in a range from 50 to 200 µm. When the thickness is below 50 µm, a sufficient electrode protection effect can not be obtained. On the other hand, when the thickness is over 200 µm, a diffusion of the exhaust gas to the electrode may be delayed, thereby the response characteristic being deteriorated.

Also, a trap layer 15 made of heat-resisting metal oxide is preferably further provided on the surface of the protective layer 14. By the trap layer 15, the adhesion strength of the protective layer 14 to the reactive electrode 12 increases and, in addition, the durability of the protective layer 14 and the reactive electrode 12 is improved. Further, the anti-poisoning characteristic thereof is also improved.

Further, the surface of the trap layer 15 preferably has a porosity of from 30 to 60%. When this porosity is below 30%, the trap layer 15 is likely to be clogged with adhered poison substances, and the response characteristic is deteriorated. On the other hand, when the porosity is over 60%, adhered poison substances are not sufficiently trapped and reach the protective layer 14, thereby causing an adverse effect thereupon.

Further, as the above-mentioned heat-resisting metal oxide, for example, $Al_2O_3$, $MgO \cdot Al_2O_3$ spinel, $ZrO_2$, $TiO_2$, or the like, or mixtures of these materials can be used.

The thickness of the trap layer 15 is preferably in a range from 10 to 100 µm. When this thickness is below 10 µm, the trap effect of the adhered poison substances may be insufficient. On the other hand, when the thickness is over 100 µm, the cost may increase and an effect corresponding to such cost increase cannot be expected.

An inside electrode 13 made of platinum is provided on the surface on the side of the standard gas of the solid electrolyte 10.

Figure 4:
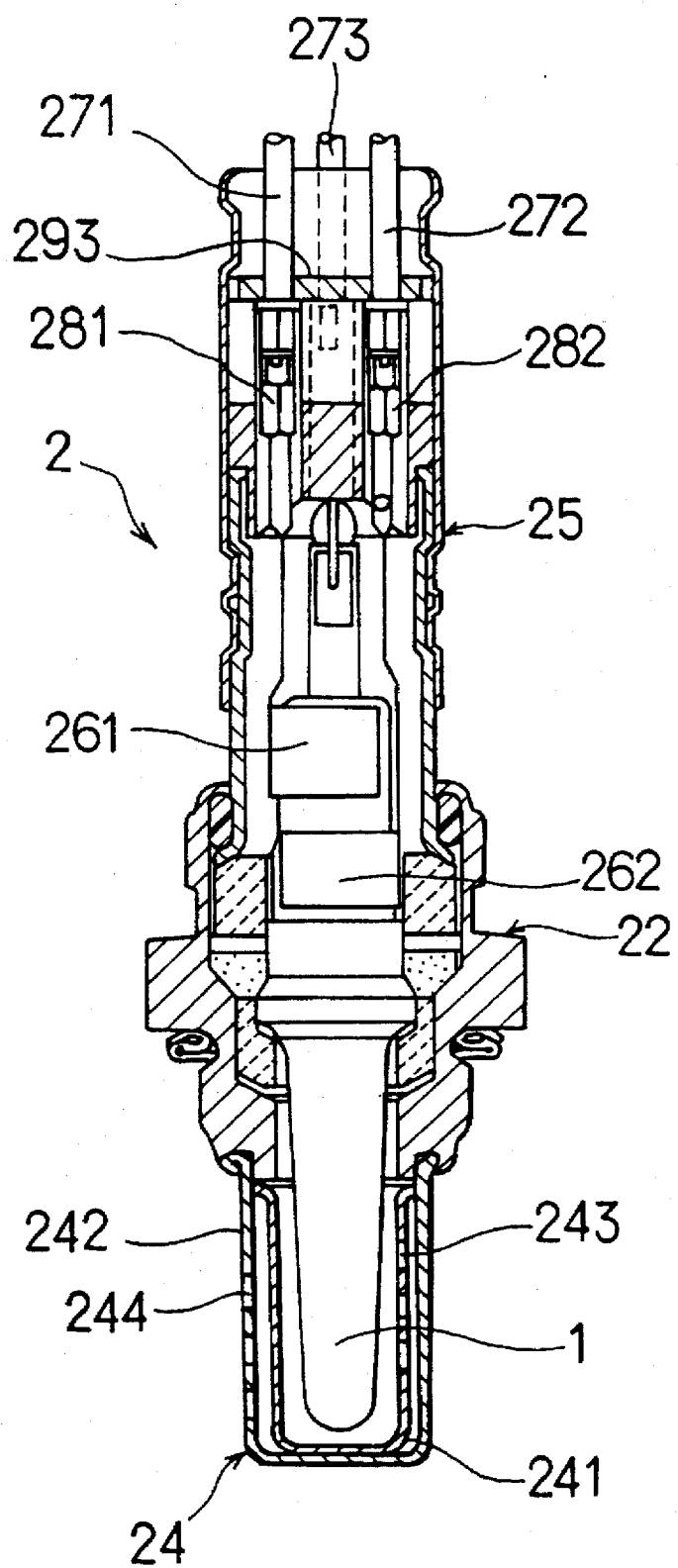
FIG. 4 is a sectional view illustrating the oxygen sensor according to the embodiment of the present invention.

Next, as illustrated in FIG. 4, an oxygen sensor 2 of this embodiment comprises the oxygen sensor element 1, a housing 22 for holding this oxygen sensor element 1, an exhaust side cover 24 provided at a lower portion of the housing 22 for covering the circumferential surface of the oxygen sensor element 1, and an atmosphere side cover 25 provided at an upper portion of the housing 22.

The oxygen sensor element 1 has two plate-like terminals 261 and 262. Lead wires 271 and 272 for outputing output-signals are connected through connectors 281 and 282 to the terminals 261 and 262, respectively. Numeral 293 denotes a bush for fixing the lead wires, numeral 241 denotes an inside cover, numeral 242 denotes an outside cover, numerals 243, 244 denote exhaust gas intake bores, and numeral 273 denotes a lead wire for energizing the heater.

Next, an operation and effect of this embodiment will be described.

In the oxygen sensor element 1 of the present invention, the reactive electrode 12 can be a thin film, because it is provided at the pore portions 19 in which the solid electrolyte 10 is exposed. Accordingly, the reactive electrode 12 can ensure the response characteristic required for the oxygen sensor 2.

Further, the pore area (SP) of each of the pore portions 19 is set to have a predetermined size in such a manner that the electrical disconnection of the reactive electrode 12 from the skeletal electrode 11 is prevented even when the reactive electrode 12 in each pore portion 19 has been aggregated by heating. Therefore, conductivity between the reactive electrode 12 and the skeletal electrode 11 is constantly maintained.

Thus, according to the first embodiment, it is possible to provide an oxygen sensor element having both excellent heat resistance and an excellent response characteristic.

Also, in this embodiment, the oxygen sensor 2 is provided with the protective layer 14 and the trap layer 15. For this reason, it is particularly possible to suppress the deterioration of the oxygen sensor 2 due to the reaction of thin film reactive electrode 12 with HC, CO, etc. which are exhaust gas components or due to the reaction of the reactive electrode 12 with Pb, P, S, etc. which are harmful components in gasoline oil.

Figure 5A:
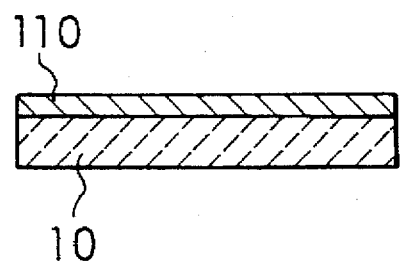
FIGS. 5A and 5B are views illustrating a first process step for manufacturing an oxygen sensor element according to the embodiment of the present invention.
Figure 5B:
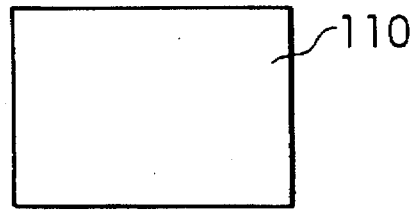

Next, a method for manufacturing the oxygen sensor element 1 will be described with respect to FIGS. 5 to 7. FIGS. 5A–7A illustrate cross sections of the solid electrolyte, etc. and FIGS. 5B–7B illustrate the surfaces thereof.

Firstly, roughening treatment is performed with respect to the surface of the cup-shaped solid electrolyte 10 by forming thereon a porous film made of the same material as that of the solid electrolyte 10, whereby this surface is irregular (concave and convex surface). Then, etching treatment is performed on the irregular surface using hydrofluoric acid.

Next, as illustrated in FIGS. 5A and 5B, a catalyst consisting of platinum or palladium is carried by the surface at the side of gas to be measured of the solid electrolyte 10, whereupon a first metal film 110 made of platinum is formed on the surface by chemical plating to a thickness of 0.8 µm.

Next, the solid electrolyte 10 is heated at a temperature of 1200° C. for one hour. As a result, the first metal film 110 gets almost melted and thereafter aggregates.

Figure 6A:
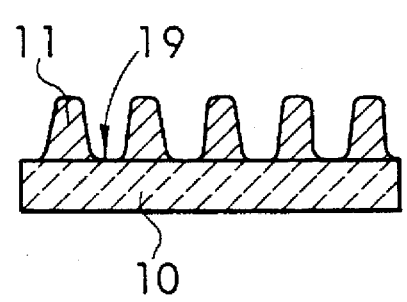
Figure 6B:
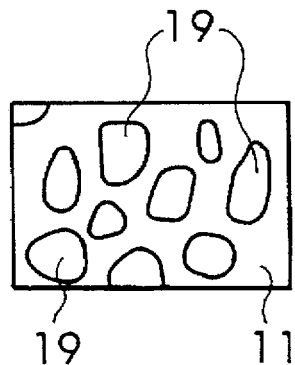
Figure 7A:
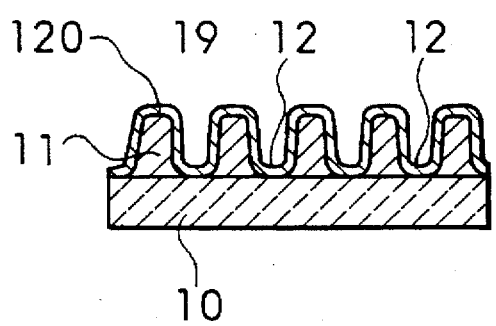
FIG. 7A and 7B are views illustrating a third process step for manufacturing the oxygen sensor element.
Figure 7B:
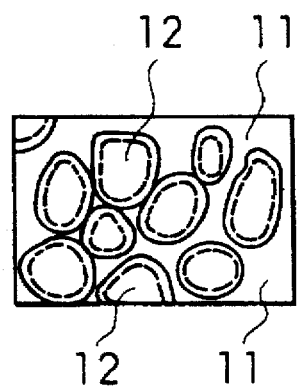

As illustrated in FIGS. 6A and 6B, the first metal film 110 gets partially thicker to a thickness of approximately 1.9 µm. At the same time, the degree of denseness increases and the skeletal electrode 11 is formed.

On the other hand, as the skeletal electrode 11 is formed, the first metal film 110 is partially lost and the pore portions 19 where the solid electrolyte 10 is exposed are formed. The area percentage (SG/SK) which is the ratio of the total pore area (SG) of the pore portions 19 to the area (SK) of the first metal film is 30%.

Thereafter, as illustrated in FIGS. 7A and 7B, a second metal film 120 having a thickness of 0.8 m is provided on the respective surfaces of the pore portions 19 and the skeletal electrode 11 by chemical plating. Of the second metal film 120, particularly the portions which cover the pore portions 19 serve as the reactive electrode 12.

The protective layer made of MgO.Al$_2$O$_3$ spinel is provided on the respective surfaces of the reactive electrode 12 and the skeletal electrode 11 by plasma spraying. The trap layer composed of particles of γ-Al$_2$O$_3$, etc. is formed on the protective layer.

The inside electrode is provided on the surface at the side of standard gas of the solid electrolyte by chemical plating.

As described above, the oxygen sensor element is obtained.

According to this method, it is possible to produce an oxygen sensor element having both an excellent heat resistance characteristic and an excellent response characteristic.

Next, the heat resistance characteristic of the oxygen sensor element according to the present invention will now be explained along with comparison examples with reference to FIG. 8.

A sample No.1 has the same structure as the oxygen sensor element 1 illustrated in FIGS. 1 and 2, the detail will be described later with respect to Table 1. Further, a sample No. C6 shown in FIG.8 as a comparison sample has the same structure as the conventional oxygen sensor element having an auxiliary lead wire shown in FIG. 9, the detail will be also described later.

When measuring the heat resistance characteristic, firstly, the sample Nos. 1 and C6 are mounted on the oxygen sensor 2 shown in FIG. 4, and each of these oxygen sensors 2 is mounted on an automobile engine. This engine is operated to emit exhaust gas, which temperature is 900° C.

If the thin film electrode 92 and reactive electrode 12 of the above-mentioned oxygen sensor element are fractured by coagulation in the form of island shape, the inner resistance of the oxygen sensor element gets higher in accordance with a decrease in the conductivity of the thin film electrode, etc.

Accordingly, the heat resistance characteristic can be evaluated by measuring the inner resistance of the oxygen sensor element of each of the samples Nos. 1 and C6.

Figure 8:
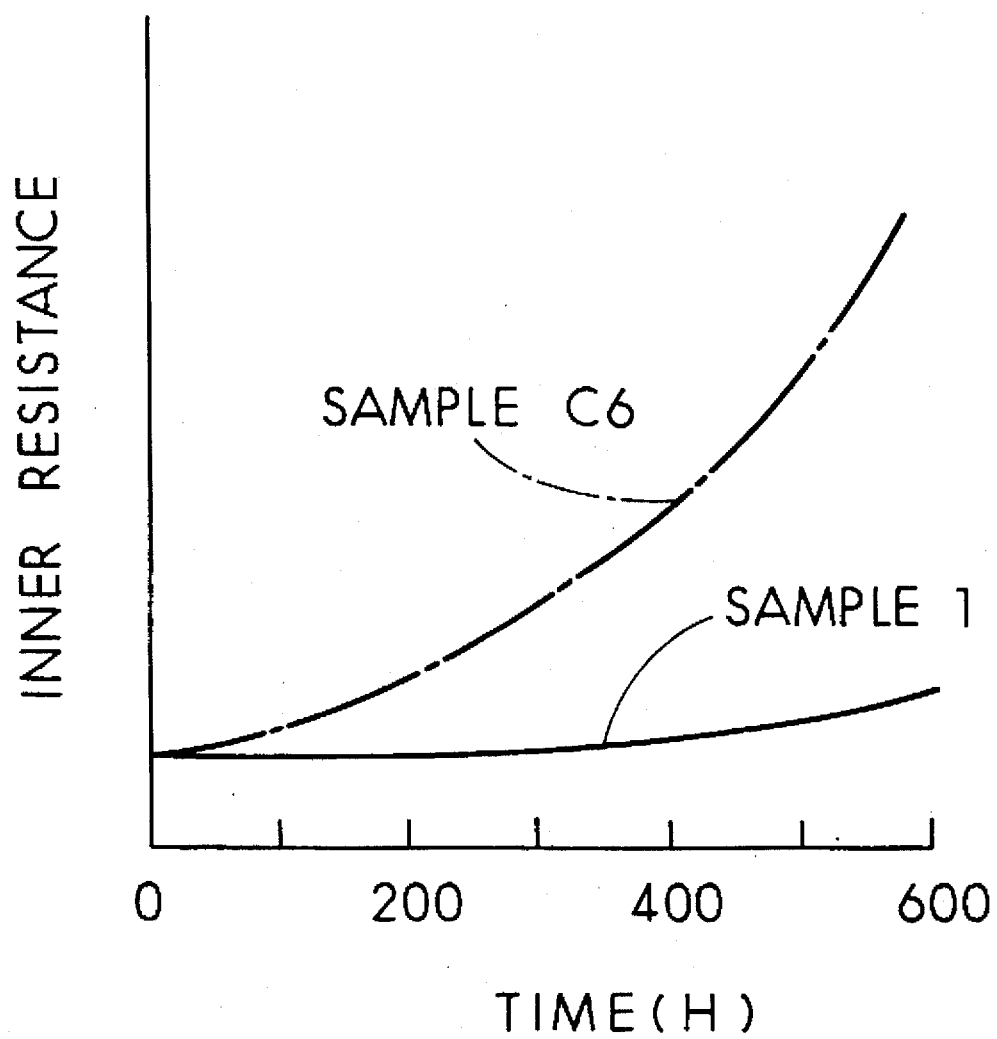
FIG. 8 is a graph showing the relationship between time passage and inner resistance of an oxygen sensor element during a heat test.

The measured results are shown in FIG. 8. In FIG.8, the abscissa represents the time passage as counted from the start of the heat test and the ordinate represents the inner resistance for samples Nos. 1 and C6.

As can be seen from FIG. 8, while the inner resistances of the samples Nos. 1 and C6 are equal immediately after the test has started, the difference between the inner resistances get larger as the test time gets longer.

Also, there is almost no change in the value of the inner resistance of the sample 1 even when the elapsed time has become 600 hours. In contrast, the inner resistance of the comparison sample No. C6 increases largely in accordance with time.

Accordingly, it is understood that the sample 1 is superior in the heat resistance, because there is almost no change in the inner resistance even after being used for long time.

The heat resistance characteristic and response characteristic of an oxygen sensor element 1 according to the present invention will now be explained along with comparison samples with reference to Tables 1 and 2.

Firstly, as shown in Tables 1 and 2, each of the samples Nos. 1 to 4 according to the present invention is the same as an oxygen sensor element 1 shown in FIGS. 1 and 2. However, the samples Nos. 1 to 4 differ from each other in the thickness of the first metal film 110 and the thickness of the second metal film 120 or in the heating temperature for forming the skeletal electrode 11. Accordingly, the samples Nos. 1 to 4 also differ from each other in the area percentage (SH/SZ) of the reactive electrode 12 as well as in the average area of the reactive electrode 12. The average area of the reactive electrode 12 is equal to the average area (SA) of the pore portions 19 formed when the skeletal electrode 11 is formed.

While the samples Nos. C1 to C3 of the comparison samples have the same structure as an oxygen sensor element 1 illustrated in FIGS. 1 and 2, the first metal film 110 of the sample No. C1 is the thinnest in thickness, the heating temperature of the sample No. C2 is the highest, and the heating temperature of the sample No. C3 is the lowest. The skeletal electrode 11 of each of the samples Nos. C1 and C2 is partially divided into separate pieces and therefore ceases to function as the skeletal electrode 11. Further, since the sample No. C3 has almost no pore portions, the area of the reactive electrode 12 is extremely small as compared to the other samples.

In each of the samples Nos. C4 and C5, the reactive electrode 12 are provided on the entire surface of the solid electrolyte 10. Accordingly, there is no structure which corresponds to the skeletal electrode 11.

Figure 9:
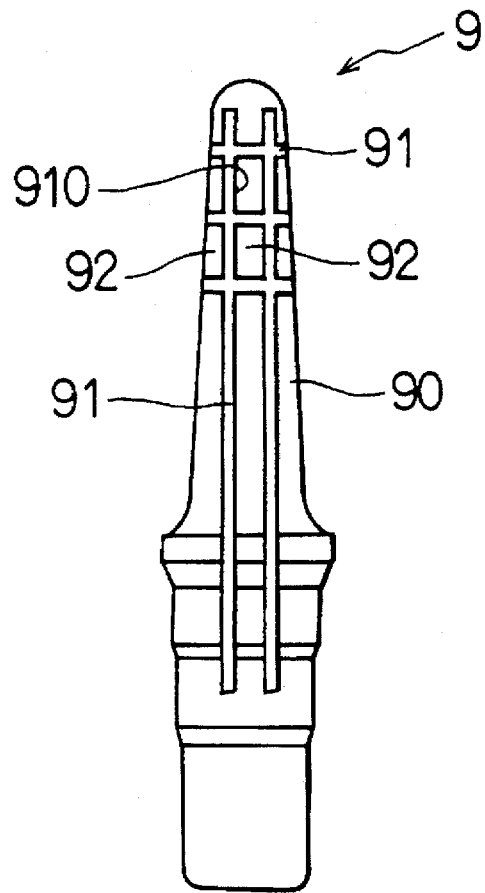
FIG. 9 is a view illustrating a conventional oxygen sensor element.
Figure 10:
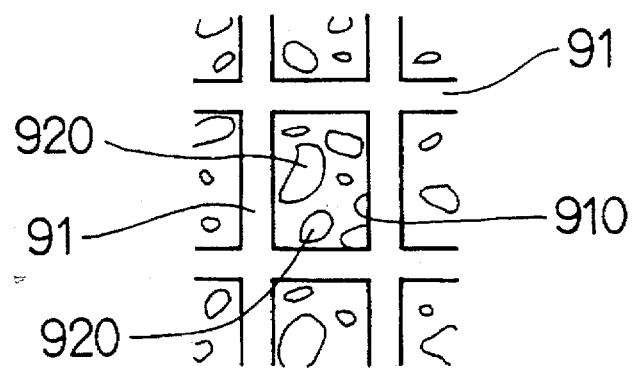
FIG. 10 is an explanatory view illustrating a main portion of the conventional oxygen sensor element shown in FIG. 9.

The sample No. C6 has the same structure as the conventional oxygen sensor element illustrated in the FIG. 9. The sample No. C6 was prepared by coating platinum paste containing boro-silicate glass onto the surface of the solid electrolyte, burning the resulting surface at a temperature of 1200° C., thereby forming the auxiliary lead, and thereafter providing a thin film of platinum on the entire surface of the solid electrolyte including the surface of the auxiliary lead by chemical plating to a thickness of 1.0 μm. The areas enclosed by the auxiliary lead form the thin film electrode.

As can be seen from Table 2, the average area of the reactive electrode in the sample No. C6 is the same as the average areas of the thin film electrode.

The measurement of the response characteristic and the heat resistance characteristic of the above-mentioned samples will now be explained.

When measuring the heat resistance characteristic, the same test, as described above (the result of which is illustrated in FIG. 8), was performed. In the cases where the inner resistance of the samples Nos. 1 to 4 and C1 to C6 is less than 50 kΩ after 500 hours has passed from the start of the test, these samples are supposed to be superior in the heat resistance characteristic (the mark o in Table 2). On the other hand, in the cases where the inner resistance is 50 kΩ or more, these samples are supposed to be inferior in the heat resistance characteristic (the mark X in Table 2).

When measuring the response characteristic, at an atmosphere temperature of 400° C., the atmosphere of the exhaust gas of the engine is switched from a rich one (λ=0.9 where X represents an excess air rate) to a lean one (λ=1.1), the time period during which the sensor output voltage changes from 0.6 V to 0.3 V is regarded as "a response time". In the cases where the response time is within 150 msec., these samples are supposed to be superior in the response characteristic (the mark o in Table 2). On the other hand, in the case where the response time is 150 msec. or more, these samples are supposed to be inferior in the response characteristic (the mark X in Table 2).

As can be understood from Table 2, each of the samples Nos. 1 to 4 in the embodiment according to the present invention is superior in both the heat resistance characteristic and the characteristic. However, although the samples Nos. C1, C2, C5, and C6 are superior in the response characteristic, they are inferior in the heat resistance characteristic. On contrary, although the samples Nos. C3 and C4 are superior in the heat resistance, they are inferior in the response characteristic.

Accordingly, it is understood that the oxygen sensor element according to this embodiment are superior in both the heat resistance characteristic and the response characteristic.

The present invention having been described should not be limited to the disclosed embodiments, but it may be modified in many other ways without departing from the scope and the spirit of the invention. Such changes and modifications are to be understood as being included with the scope of the present invention as defined by the appended claims.

TABLE 1

| | | Manufacturing Method for Electrodes | | |
|---|---|---|---|---|
| | | Skeletal Electrode | | Reactive Electrode |
| SAMPLE NO. | | Thickness of First Metal Film (μm) | Heating Temperature (°C.) | Thickness of Second Metal Film (μm) |
| Present Invention | 1 | 0.7 | 1100 | 0.7 |
| | 2 | 0.8 | 1200 | 0.8 |
| | 3 | 1.0 | 1200 | 1.0 |
| | 4 | 1.3 | 1300 | 1.3 |
| Comparison Samples | C1 | 0.5 | 1200 | 0.8 |
| | C2 | 0.8 | 1400 | 0.8 |
| | C3 | 1.0 | 1000 | 0.6 |
| | C4 | — | — | 1.6 |
| | C5 | — | — | 1.0 |
| | C6 | Paste Coated and Baked | | 1.0 |

TABLE 2

| SAMPLE NO. | | Construction of Electrode | | | | | |
|---|---|---|---|---|---|---|---|
| | | Thickness of Skeletal Electrode (μm) | Thickness of Reactive Eelectrode (μm) | Area Percentage of Reactive Electrode (%) | Average Area of Reactive Electrode (μm) | Heat Resistance Characteristic | Response Characteristic |
| Present Invention | 1 | 1.6 | 0.7 | 20 | 12 | ○ | ○ |
| | 2 | 1.9 | 0.8 | 30 | 18 | ○ | ○ |
| | 3 | 2.3 | 1.0 | 20 | 14 | ○ | ○ |
| | 4 | 3.2 | 1.3 | 20 | 20 | ○ | ○ |
| Comparison Samples | C1 | 2.5 | 0.8 | 70 | — | x | ○ |
| | C2 | 3.5 | 0.8 | 70 | — | x | ○ |
| | C3 | 1.6 | 0.6 | 1 | 0.1 | ○ | x |
| | C4 | — | 1.6 | 100 | — | ○ | x |
| | C5 | — | 1.0 | 100 | — | x | ○ |
| | C6 | 20 | 1.0 | 100 | 5 mm² | x | ○ |

What is claimed is:

1. An oxygen sensor element comprising:

a solid electrolyte having a side surface at one side thereof, said side surface being contactable with a gas to be measured;

a skeletal electrode provided on said side surface and having a plurality of pore portions, each of said pore portions passing through said skeletal electrode up to said solid electrolyte; and a reactive electrode made of a porous film provided in each of said pore portions and disposed directly on said solid electrolyte, a thickness of said porous film being smaller than that of said skeletal electrode, wherein an area percentage (SH/SZ) which is a ratio of a total area (SH) of said reactive electrode to a total area (SZ) of said skeletal electrode and said reactive electrode is in a range from 10 to 50%, an average of an area (SA) of said pore portions in which said reactive electrode disposed directly on said solid electrolyte exists, surrounded by said skeletal electrode, is 100 μm² or less, a film thickness of said skeletal electrode is in a range from 1.5 to 4 μm, and said film thickness of said reactive electrode is in a range from 0.6 to 1.5 μm.

2. An oxygen sensor element according to claim 1, wherein a surface roughness Rz on said side surface of said solid electrolyte is in a range from 30 to 60 μm.

3. An oxygen sensor element according to claim 1, wherein said reactive electrode is provided only in said pore portions.

4. An oxygen sensor element according to claim 1, wherein said skeletal electrode includes a portion of said reaction electrode formed in a region other than said pore portions.

5. An oxygen sensor element comprising:

a solid electrolyte having a side surface at one side thereof, said side surface being contactable with a gas to be measured;

a skeletal electrode provided on said side surface and having a plurality of pore portions, each of said pore portions passing through said skeletal electrode up to said solid electrolyte; and a reactive electrode made of a porous film provided in each of said pore portions and disposed directly on said solid electrolyte, a thickness of said porous film being smaller than that of said skeletal electrode, wherein 80% or more of said pore portions in which said reactive electrode exists have an average area of 100 μm² or less, an average percentage (SH/SZ) which is a ratio of a total area (SH) of said reactive electrode provided in said pore portions having an area of 100 μm² or less to a total area (SZ) of said skeletal electrode and said reactive electrode provided in said pore portions having an area of 100 μm or less is in a range from 10 to 50%, a film thickness of said skeletal electrode is in a range from 1.5 to 4 μm, and said film thickness of said reactive electrode is in a range from 0.6 to 1.5 μm.

6. An oxygen sensor element according to claim 5, wherein a surface roughness Rz on said side surface of said solid electrolyte is in a range from 30 to 60 μm.

7. An oxygen sensor element according to claim 5, wherein said reactive electrode is provided only in said pore portions.

8. An oxygen sensor element according to claim 5, wherein said skeletal electrode includes a portion of said reaction electrode formed in a region other than said pore portions.

9. A method of manufacturing an oxygen sensor element having a solid electrolyte, said method comprising:

a step of forming a first metal film on a surface of said solid electrolyte at the side of a gas to be measured;

a step of forming pore portions on said first metal film by coagulating said first metal in such a manner that said pore portions pass from a surface of said first metal film to said solid electrolyte; and a step of forming a second metal film on said surface of said first metal film, which have been covered with said pore portions.

10. A method according to claim 9, wherein said second metal film provided in said pore portions is a reactive electrode having a thickness from 0.6 to 1.5 μm.

11. A method according to claim 9, wherein said first metal film and said second metal film provided on said first metal film are a skeletal electrode having a thickness from 1.5 to 4 μm.

12. A method according to claim 9, wherein said pore portions have an area percentage (SG/SK) from 10 to 50%, which is a ratio of a total area (SG) of said pore portions to an area (SK) of said first metal film.

13. A method according to claim 9, wherein at least 80% of said pore portions have an area of 100 $\mu m^2$ or less.

14. A method according to claim 13, wherein an area percentage (SH/SZ) which is a ratio of a total area (SH) of said reactive electrode provided in said pore portions having an area of 100 $\mu m^2$ or less to an area (SZ) of said skeletal electrode and said reactive electrode provided in said pore portions having an area of 100 $\mu m^2$ or less is in a range from 10 to 50%.

15. A method according to claim 9, wherein an average area of said pore portions is 100 $\mu m^2$ or less.

16. A method according to claim 9, further comprising:

a step of performing surface roughening treatment of a surface roughness Rz=30 to 60 $\mu m$ on said surface of said solid electrolyte; and a step of performing etching treatment on said surface of said solid electrolyte, wherein said surface roughening treatment and said etching treatment are performed before said first metal film are formed.

17. A method according to claim 9, wherein said first metal film is aggregated by heating said first metal film.

18. A method according to claim 17, wherein said heating for coagulating said first metal film is performed at or more than a set temperature in which said skeletal electrode does not re-aggregate during an operation of said oxygen sensor element.

* * * * *